United States Patent
Narayanaswamy et al.

(10) Patent No.: US 11,680,028 B2
(45) Date of Patent: Jun. 20, 2023

(54) METHODS AND SYSTEMS FOR UPGRADING CRUDE OILS, HEAVY OILS, AND RESIDUES

(71) Applicant: SABIC Global Technologies B.V., Bergen op Zoom (NL)

(72) Inventors: Ravichander Narayanaswamy, Karnataka (IN); Hatem Belfadhel, Riyadh (SA); Girish Koripelly, Bangalore (IN); Alexander Stanislaus, Bangalore (IN); Krishna Kumar Ramamurthy, Bengaluru (IN); Krishnan Sankaranarayanan, Missouri City, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/422,784

(22) PCT Filed: Jan. 16, 2020

(86) PCT No.: PCT/IB2020/050358
§ 371 (c)(1),
(2) Date: Jul. 14, 2021

(87) PCT Pub. No.: WO2020/157595
PCT Pub. Date: Aug. 6, 2020

(65) Prior Publication Data
US 2022/0064084 A1    Mar. 3, 2022

Related U.S. Application Data

(60) Provisional application No. 62/798,396, filed on Jan. 29, 2019.

(51) Int. Cl.
*C07C 4/06* (2006.01)
*B01D 3/14* (2006.01)
(Continued)

(52) U.S. Cl.
CPC ............... *C07C 4/06* (2013.01); *B01D 3/14* (2013.01); *C07C 2/84* (2013.01); *C07C 4/04* (2013.01); *C07C 7/04* (2013.01); *C07C 2523/883* (2013.01)

(58) Field of Classification Search
CPC ........ C10G 2300/206; C10G 2300/807; C10G 2400/20; C10G 47/26; C10G 69/06;
(Continued)

(56) References Cited

U.S. PATENT DOCUMENTS

| 4,462,895 A | 7/1984 | Biceroglu et al. |
| 4,557,821 A | 12/1985 | Lopez et al. |

(Continued)

FOREIGN PATENT DOCUMENTS

| CN | 104560177 A | 4/2015 |
| CN | 105473691 A | 4/2016 |

(Continued)

OTHER PUBLICATIONS

Joshi, et al.: "Petroleum Residue Upgradation via Visbreaking: A Review", Ind. Eng. Chem. Res. 47 (2008), pp. 8960-8900.
(Continued)

*Primary Examiner* — Sharon Pregler
(74) *Attorney, Agent, or Firm* — Norton Rose Fulbright US LLP (57) ABSTRACT

Systems and methods for producing olefins and/or aromatics are disclosed. Methods disclosed includes aqua-processing hydro-processing of crude oils and/or heavy oils and/or residue, in an aqua-processing hydro-processing unit, to produce intermediate products, which can then be used to make valuable chemicals such as olefins and aromatics.

20 Claims, 4 Drawing Sheets

(51) Int. Cl.
*C07C 2/84* (2006.01)
*C07C 4/04* (2006.01)
*C07C 7/04* (2006.01)

(58) Field of Classification Search
CPC ....... C10G 9/36; C07C 2523/883; C07C 2/84; C07C 4/04; C07C 4/06; C07C 7/04
See application file for complete search history.

(56) References Cited

U.S. PATENT DOCUMENTS

| | | | |
|---|---|---|---|
| 5,080,777 | A | 1/1992 | Aegerter, Jr. et al. |
| 5,688,395 | A | 11/1997 | Carrazza et al. |
| 5,885,441 | A | 3/1999 | Pereira et al. |
| 6,171,473 | B1 | 1/2001 | Fornoff |
| 9,115,318 | B2 | 8/2015 | Al-Abdulal et al. |
| 9,168,506 | B2 | 10/2015 | Caneion et al. |
| 9,284,501 | B2 * | 3/2016 | Sayed ................ C10G 49/007 |
| 10,689,587 | B2 * | 6/2020 | Al-Sayed ............... C10G 45/00 |
| 2007/0090018 | A1 | 4/2007 | Keusenkothen et al. |
| 2007/0090019 | A1 | 4/2007 | Keusenkothen et al. |
| 2013/0197285 | A1 | 8/2013 | Shafi et al. |
| 2013/0248418 | A1 | 9/2013 | Sayed et al. |
| 2015/0144527 | A1 | 5/2015 | Fathi |
| 2016/0122668 | A1 | 5/2016 | Sayed et al. |
| 2016/0137933 | A1 | 5/2016 | Ward et al. |
| 2017/0015916 | A1 | 1/2017 | Oprins et al. |
| 2018/0187099 | A1 | 7/2018 | Bourane et al. |
| 2018/0312767 | A1 | 11/2018 | Al-Sayed et al. |

FOREIGN PATENT DOCUMENTS

| | | |
|---|---|---|
| CN | 106164224 A | 11/2016 |
| CN | 107118801 A | 9/2017 |
| CN | 107916128 A | 4/2018 |
| CN | 113710776 A | 11/2021 |
| EP | 3110913 A1 | 1/2017 |
| EP | 3110914 A1 | 1/2017 |
| WO | WO2013126364 A2 | 8/2013 |
| WO | WO2015128043 A1 | 9/2015 |
| WO | WO2018142351 A1 | 8/2018 |

OTHER PUBLICATIONS

International Search Report and Written Opinion from PCT/IB2020/050613 dated Mar. 16, 2020, 8 pages.
Corma et al. "Crude oil to chemicals: light olefins from crude oil." Catalysis Science and Technology, vol. 7 (2017), 86 pages.
Corma et al. "Direct crude oil cracking for producing chemicals: Thermal cracking modeling." Fuel, vol. 211 (2018) 726-736.
Fathi et al. "Catalytic Aquaprocessing of Arab Light Vacuum Residue via Short Space Times." Energy Fuels 2011, 25, 4867-4877.
Fathi et al. "Kinetic Modeling of Arab Light Vacuum Residue Upgrading by Aquaprocessing at High Space Velocities." Ind. Eng. Chem. Res. 2013, 52, 612-623.
Fathi, M. M. A. "Comparative upgrading of arab light vacuum residuum via aquaprocessing and thermal cracking." Thesis, Department of Chemical and Petroleum Engineering, University of Calgary, Sep. 2011, prism.ucalgary.ca, doi: http://dx.doi.org/10.5072/PRISM/4384.
Garcia-Hubner, E.A., "Catalysts Evaluation for Catalytic Steam Cracking of De-Asphalted Oil in a Fixed Bed Reactor," Thesis for Degree of Master of Science, Graduate Program in Chemical Engineering, University of Calgary, Nov. 2015.
International Search Report and Written Opinion from PCT/IB2020/050358 dated Mar. 16, 2020, 11 pages.

* cited by examiner

METHODS AND SYSTEMS FOR UPGRADING CRUDE OILS, HEAVY OILS, AND RESIDUES

CROSS REFERENCE TO RELATED APPLICATIONS

This application is a national phase application under 35 U.S.C. § 371 of International Application No. PCT/IB2020/050358 filed Jan. 16, 2020, which claims priority to U.S. Provisional Patent Application No. 62/798,396 filed Jan. 29, 2019. The entire contents of each of the above-referenced disclosures is specifically incorporated by reference herein without disclaimer.

FIELD OF INVENTION

The present invention generally relates to the refining of crude oil and/or heavy oil and/or residues. More specifically, the present invention relates to the aqua-processing hydro-processing of crude oils and/or heavy oils and/or residues to produce intermediate products, which can then be used to make valuable chemicals such as olefins and aromatics.

BACKGROUND OF THE INVENTION

The conversion of whole petroleum crude oil to chemicals practiced in the art includes the use of a series of hydrocrackers, fluid catalytic crackers (FCCs) and steam crackers to produce either high value chemicals only or a combination of high value chemicals and fuels. However, hydrocracking, fluid catalytic cracking, and steam cracking processes involve problematic upgrading of heavy ends of crude oils using multi-step processes such as resid hydrocracking, coking, middle distillate hydrocracking, naphtha range hydrocracking etc., before actually feeding hydrocarbons to final conversion units like steam crackers or FCCs to produce olefins and/or aromatics.

Further, the hydro-processing conditions employed involve high pressures, up to 200 barg, which require high investment costs in equipment. Because upgrading involves using multiple feed preparation units, e.g., hydrocrackers, cokers, and hydrotreaters, at each stage, not only is there a forced cracking of molecules and addition of $H_2$ for satisfying the hydrogen deficiency introduced as a result of cracking at each stage, there is also a preheating of the feed to operating temperatures by feed preheat furnaces for each of these feed preparation units. This results in the consumption of large amounts of fuel on the utility side as well. Hence, there is a need for feed upgradation and conversion to chemicals using a more intensified process that employs a minimum number of processing units and employs processes that convert the crude oil in an optimal manner to feeds for the downstream conversion unit. The downstream conversion units convert the feeds to high value chemicals; and it is desirable that this is done with a preference for maximizing ethylene while producing propylene and benzene.

BRIEF SUMMARY OF THE INVENTION

A discovery has been made that provides a solution to at least some of the problems associated with processing crude oils and/or heavy oils and/or residues. The solution is premised on a sophisticated process that uses hydrogen and steam to efficiently upgrade crude oils and/or heavy oils and/or residues in the presence of a catalyst. The upgraded products are then fed to conversion units that convert these upgraded products to olefins and aromatics such as ethylene, propylene, butene, and benzene.

Embodiments of the invention include a method of processing hydrocarbons of crude oils and/or heavy oils and/or residues. The method includes subjecting a mixture comprising (1) a feedstock of crude oil and/or heavy oil and/or residues, (2) steam, (3) hydrogen, (4) catalyst(s), and (5) a solvent selective for dissolving asphaltene, in a processing unit, to conditions sufficient to convert at least some hydrocarbon molecules of the feedstock to molecules that have less carbon atoms than the at least some hydrocarbon molecules. The method further includes recovering, from the processing unit, intermediate product streams comprising: (1) a gas stream that comprises primarily $C_1$ to $C_4$ hydrocarbons and (2) a liquid stream that comprises primarily saturates. Further yet, the method includes cracking the liquid stream to produce one or more of ethylene, propylene, butene, and benzene.

Embodiments of the invention include a method of processing hydrocarbons of crude oil and/or heavy oil and/or residues. The method of aqua-processing hydro-processing includes flowing (1) a feedstock of crude oil and/or heavy oil and/or residues, (2) steam, (3) hydrogen, (4) catalyst(s), and (5) a solvent selective for dissolving asphaltene to a processing unit, the processing unit comprising (a) a reactor unit that comprises a plurality of reactors and (b) a separation unit comprising a distillation column. The method further includes subjecting a mixture comprising the feedstock of crude oil and/or heavy oil and/or residues, the steam, a first portion of the hydrogen, a first portion of the catalyst(s), and a first portion of the solvent in a first reactor of the plurality of reactors, to reaction conditions sufficient to convert at least some hydrocarbon molecules of the feedstock to molecules that have less carbon atoms than the at least some hydrocarbon molecules of the feedstock. In embodiments of the method, solvent is provided in the mixture in a quantity sufficient to keep at least 90 wt. % of asphaltenes from the feedstock in solution so that asphaltenes do not crash out during the course of conversion. The method further yet includes flowing first reactor effluent from the first reactor to a second reactor of the plurality of reactors and subjecting the first reactor effluent, a second portion of the hydrogen, a second portion of the catalyst(s), and a second portion of the solvent, in the second reactor of the plurality of reactors, to reaction conditions sufficient to convert at least some hydrocarbon molecules of the first reactor effluent to molecules that have less carbon atoms than the at least some hydrocarbon molecules of the first reactor effluent. The construct of the plurality of reactors can, in fact, be a single large reactor (a tubular reactor, bubble column reactor, jet loop reactor, or other types) with staged injection of solvent, hydrogen and catalyst(s) along its length. The method also includes flowing reactor unit effluent from the reactor unit to the distillation column of the separation unit and distilling, in the distillation column, the reactor unit effluent, to produce streams comprising: (1) a gas stream that comprises primarily $C_1$ to $C_4$ saturates, (2) a liquid product stream that comprises primarily saturates. The method may also include removing coke from the reactor unit. The method further includes cracking, in a steam cracker, the liquid product stream to produce one or more of ethylene, propylene, butene, and benzene.

The following includes definitions of various terms and phrases used throughout this specification.

The term "crude oil," as that term is used in the specification and/or claims, means oil from underground that has not been processed to make products such as gasoline, naphtha, kerosene, gasoil, and residue. Crude oil can have a gravity of 4 to 80° API, more typically 15 to 45° API.

The term "heavy oil," as that term is used in the specification and/or claims, means a portion of the crude oil that boils above 350° C., which could be generated as bottoms of crude oil atmospheric tower, or a vacuum gas oil portion of the crude oil that boils from 350° C. to 550° C. generated in a crude oil vacuum tower, or vacuum residue portion that boils above 550° C. generated as a bottoms of crude oil vacuum tower.

The term "residual" (or "resid") as that term is used in the specification and/or claims, means a mixture of petroleum compounds including aromatics, paraffins, sulfur, nitrogen metals which is generated from the whole crude oil by removing materials boiling below a certain boiling point. For example, a 120+° C. residue is generated as a bottoms when whole crude oil is distilled to remove hydrocarbons boiling below 120° C.

The term "saturates" refers to hydrocarbons of the type paraffins, isoparaffins, and naphthenes alone or in any combination.

The term "resin" refers to hydrocarbons with more than 3 to 4 aromatic rings with and without side chains and with or without naphthenic species.

The term "asphaltenes" refers to molecules with island and archipelago structures and also molecules with polycyclic rings with and without heteroatoms.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for upgrading whole crude oils, and/or heavy oils and/or residues, which involves using hydrogen and steam in the presence of dissolved and dispersed catalyst in an aqua-processing hydro-processing unit. The upgraded products are then converted to olefins such as ethylene, propylene, and butene and aromatics such as benzene.

Figure 1:
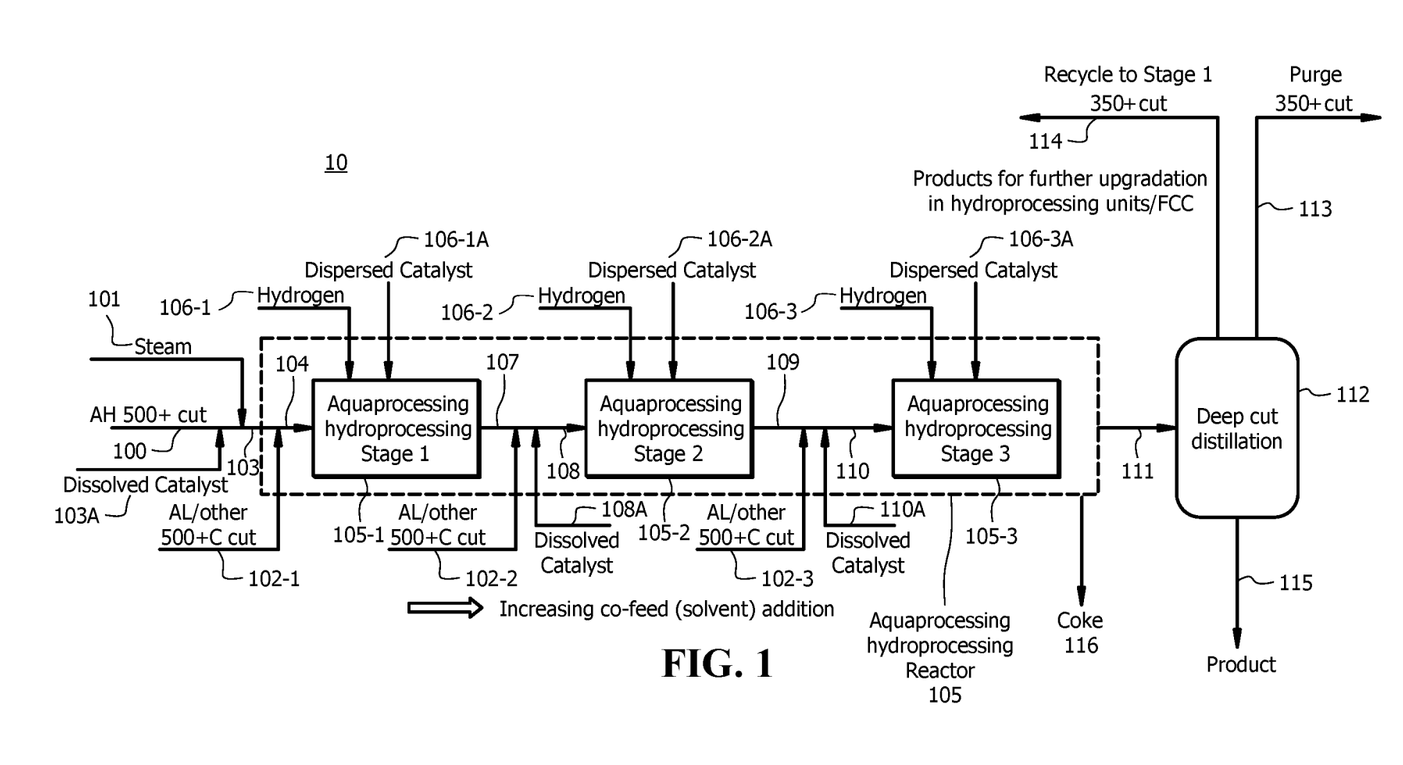
FIG. 1 is a system for aqua-processing hydro-processing crude oil and/or heavy oil and/or residues, according to embodiments of the invention.
Figure 2:
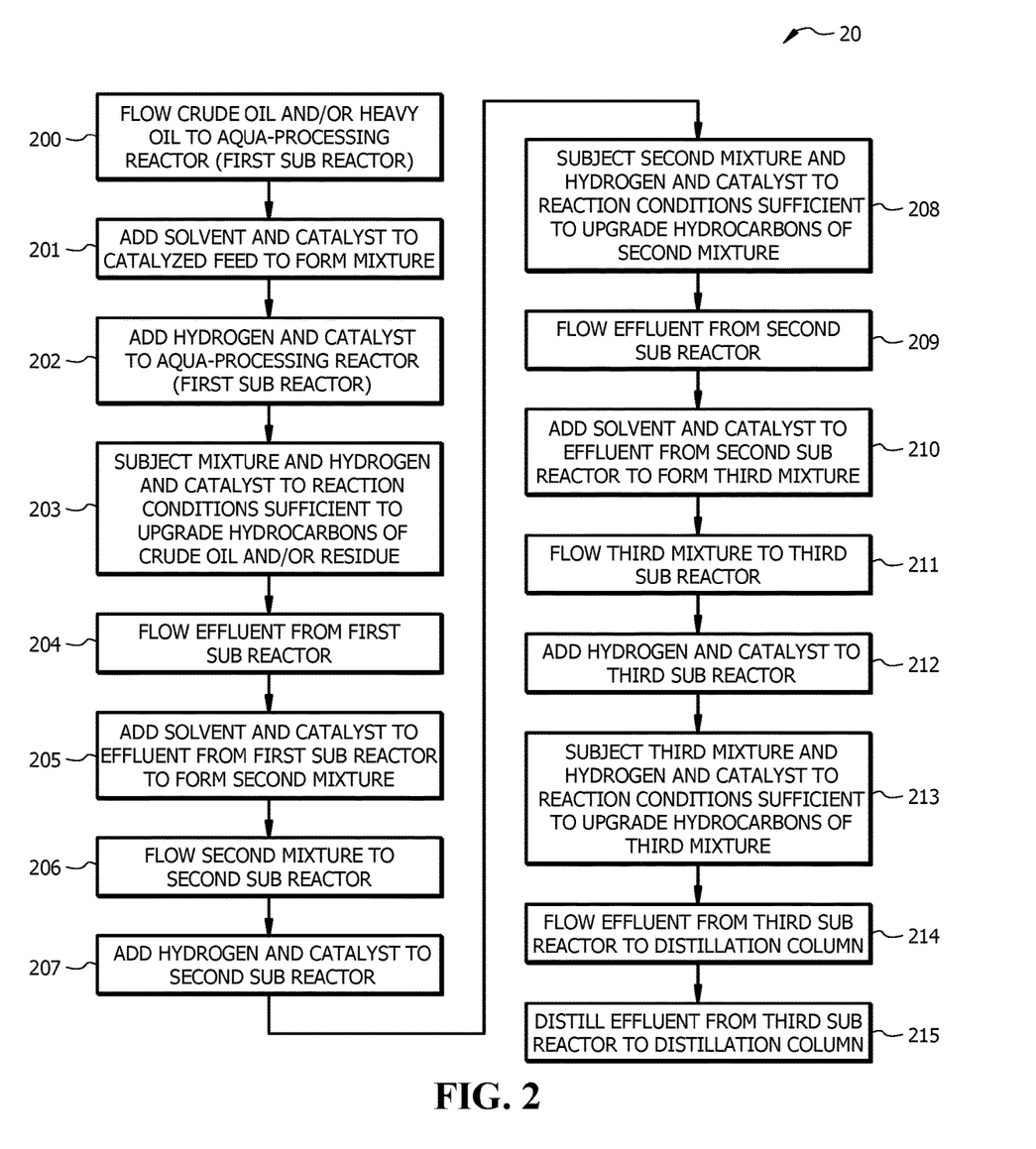
FIG. 2 is a method for aqua-processing hydro-processing crude oil and/or heavy oil and/or residues, according to embodiments of the invention.

FIG. 1 shows system 10 for aqua-processing hydro-processing crude oil and/or heavy oil and/or residues, according to embodiments of the invention. FIG. 2 shows method 20 for aqua-processing and hydro-processing crude oil and/or heavy oil, according to embodiments of the invention. Method 20 may be implemented using system 10.

Table A shows the properties of AH 500+ cut and AL 500+ cut shown in FIG. 1. It should be noted that embodiments of the invention can include values for the properties that are in a range within 10% of the values shown in Table A.

TABLE A

| Properties | AL 500+° C. cut | AH 500+° C. cut |
|---|---|---|
| API Gravity | 9.5 | 5.5 |
| Density (g/cc) | 1.0024 | 1.0223 |

TABLE A-continued

| Properties | AL 500+° C. cut | AH 500+° C. cut |
| --- | --- | --- |
| K factor | 11.64 | 11.56 |
| Total Sulphur, wt. % | 4.09 | 5.32 |
| Total Nitrogen, ppm | 2209 | 2861 |
| Conradson Carbon Residue, wt. % | 17.2 | 21.91 |
| Asphaltenes, wt. % | 6.39 | 14.69 |

According to embodiments of the invention, method 20 involves, at block 200, flowing feed 100 (crude oil and/or heavy oil and/or residues) to aqua-processing hydro-processing reactor 105. In embodiments of the invention, feed 100 comprises AH 500+° C. According to embodiments of the invention, AH 500+° C. cut has the following properties: 5.0 to 6.0 API gravity, 0.92007 to 1.12453 density (g/cc), 10.404 to 12.716 K factor, 4.788 to 5.852 wt. % total sulphur, 2574.9 to 3147.1 ppm total nitrogen, 19.72 to 24.10 wt. % Conradson carbon residue, 13.22 to 16.16 wt. % asphaltenes. Block 200 in embodiments of the invention, includes combining feed 100 with steam 101 and dissolved catalyst stream 103A to form catalyzed feed 103. According to embodiments of the invention, steam is provided at a flow rate required to supply at least more than 0.2 wt. % hydrogen with respect to feed 100. In embodiments of the invention, steam can pass at ½ of the feed wt. % and if the contribution of hydrogen is 10% of the total hydrogen from water, it accounts for approximately 0.2%. In embodiments of the invention, steam/water stream 101 is introduced in the ratio of 0 to 1 wt./wt. of feed hydrocarbon liquid. Dissolved catalyst (dissolved catalyst stream 103A, dissolved catalyst stream 108A, and dissolved catalyst stream 110A) may be metal organic salts in hydrocarbon base. Dispersed catalyst in the form of a slurry or fixed bed catalyst can also be used in the reactor. In embodiments of the invention, where dispersed catalyst stream 106-1A, dispersed catalyst stream 106-2A, or dispersed catalyst stream 106-3A is a slurry, then it is present in a hydrocarbon base. In embodiments of the invention, the dissolved catalyst is an organometallic compound of nickel (Ni), molybdenum (Mo), cobalt (Co) or other metal naphthenates or octanoates having hydrogenation activity. The dissolved catalyst addition in each of sub reactor 105-1, sub reactor 105-2, and sub reactor 105-3 is targeted so as to get 0-15000 ppmw of each metal in mixture 104, mixture 108, and mixture 110. The dispersed catalyst can be, according to embodiments of the invention, an alkali metal hydroxide or oxide, Ni—Mo oxides or sulphides, Co—Mo oxides or sulphides, W—Mo oxides or sulphides on alumina or zeolites or any combination of these having hydro-processing and/or hydrogen transfer activity. In embodiments of the invention, 0.1 to 15 wt. % content of each type of metal may be present in the dispersed catalyst and supported on alumina, silica or aluminosilcates/zeolites and the metals may be present as oxides or sulphides.

According to embodiments of the invention, catalyzed feed 103 may be at a temperature, entering aqua-processing hydro-processing reactor 105, in a range of 25 to 500° C. As an alternative to or in addition to mixing feed 100 and steam 101 and dissolved catalyst stream 103A to form catalyzed feed 103 outside of aqua-processing hydro-processing reactor 105, in embodiments of the invention, feed 100 may be combined with steam 101 and dissolved catalyst stream 103A, within aqua-processing hydro-processing reactor 105 (which can be one reactor or can comprise a plurality of sub reactors).

According to embodiments of the invention, aqua-processing hydro-processing reactor 105 comprises a plurality of sub reactors that implement a plurality of stages in aqua-processing hydro-processing reactor 105. As shown in FIG. 1, aqua-processing hydro-processing reactor 105 may comprise sub reactor 105-1, sub reactor 105-2, and sub reactor 105-3, where each sub reactor implements an aqua-processing stage in aqua-processing hydro-processing reactor 105.

According to embodiments of the invention, at block 201, solvent 102-1 is added to catalyzed feed 103 to form mixture 104, which is fed to aqua-processing hydro-processing reactor 105 (specifically sub reactor 105-1). Alternatively or additionally, in embodiments of the invention, catalyzed feed 103, or components thereof, may be combined with solvent 102-1 within aqua-processing hydro-processing reactor 105 (specifically sub reactor 105-1). According to embodiments of the invention, solvent 102-1 is used to dissolve and keep asphaltenes in solution. In embodiments of the invention, solvent 102-1 comprises primarily aromatics and/or resin. In embodiments of the invention, solvent 102-1 comprises crude oil rich in aromatics (e.g., Arab Light crude oil, Arab Heavy crude oil), pyrolysis gasoline and other cracked liquid products from steam cracker, cycle oils from fluid catalytic cracker, coker liquid products, or combinations thereof. Other solvents, for use in embodiments of the invention, may be swelling solvents like acetone, acetonitrile, methanol, ethyl acetate, and combinations thereof. It should be noted that the addition of solvent 102-1 to catalyzed feed 103 and/or to the mixture in sub reactor 105-1 prevents asphaltenes from crashing out of solution (precipitating) during the operation.

At block 202, in embodiments of the invention, hydrogen stream 106-1 and dispersed catalyst stream 106-1A are added to sub reactor 105-1. In embodiments of the invention, organometal salts are added to feed/solvent stream to ensure that the concentration of metal is 0-15000 ppmw of mixture 104, mixture 108, and/or mixture 110 when solvent stream 102-1, solvent stream 102-2, and solvent stream 102-3 is introduced. In embodiments of the invention, hydrogen is added in the ratio of 0 to 3000 NL $H_2$/L of feed 104/108/110 with a reactor pressure in 105-1, 105-2, 105-3 being in the range of 0 to 200 barg and more preferably in the range of 10 to 70 barg. In embodiments of the invention, hydrogen stream 106-1 comprises a pure hydrogen gas from steam methane reformer or a hydrogen grid or a hydrogen rich stream such as fuel gas stream, cracked gas coming from any refinery/petrochemical unit. Fuel gas can comprise $H_2$, $C_1$, $C_2$ and to some extent $C_3$. In embodiments of the invention, it is preferable to have hydrogen stream 106-1 comprising greater than 50 wt. % $H_2$. The catalyst of catalyst stream 106-1A may be a selection from: an alkali metal hydroxide or oxide, Ni—Mo oxides or sulphides, Co—Mo oxides or sulphides, W—Mo oxides or sulphides on alumina or zeolites or any combination of these having hydro-processing and/or hydrogen transfer activity. In embodiments of the invention, 0.1 to 15 wt. % content of each type of metal may be present in the dispersed catalyst and supported on alumina, silica or aluminosilcates/zeolites and the metals may be present as oxides or sulphides. According to embodiments of the invention, hydrogen stream 106-1 may be at a temperature, entering aqua-processing hydro-processing reactor 105, in a range of 50 to 550° C.

According to embodiments of the invention, at block 203, a mixture of mixture 104, hydrogen stream 106-1, and dispersed catalyst 106-1A is subjected to reaction conditions in sub reactor 105-1 sufficient to upgrade feed 100. In this way, hydrocarbon molecules of feed 100 are converted into smaller molecules. According to embodiments of the invention, the upgrading process can be carried out in sub reactor 105-1 at a temperature in a range of 300 to 550° C., preferably in a range of 400 to 470° C.; at a pressure of up to 200 barg, preferably a pressure of 70 barg or less. Here, the process involves treating the whole crude oil or heavy oil or residues with steam, co-feed (solvent) and catalyst under pressure of hydrogen, which converts the whole crude oil or heavy oil into lighter compounds such as distillates. Including hydrogen in aqua-processing hydro-processing reactor 105 (specifically sub reactor 105-1) as disclosed herein also has the effect of reducing coke formation and results in higher carbon efficiency. According to embodiments of the invention, the inclusion of water/steam in the reactor can have the benefit of reducing coke formation.

During the operation, the dissolved catalyst undergoes in-situ transformation into species such as organic sulfide that are active towards hydrogen uptake. The dispersed catalyst facilitates hydrogen transfer and supports hydro-processing activity. The use of steam with feed 100 helps in boiling point reduction of products and also has a benefit of reducing coke formation.

At block 204, according to embodiment of the invention, effluent 107 is flowed from sub reactor 105-1. According to embodiments of the invention, conversion of 350+° C. material present in the feed (mixture) to each of sub reactor 105-1, sub reactor 105-2, sub reactor 105-3 is converted to 350–° C. material up to an extent of 100%, alternatively 90%, 80%, 70% and not less than 60%. This conversion can be achieved by sub reactor 105-1, sub reactor 105-2, and/or sub reactor 105-3.

In embodiments of the invention, method 20 involves, at block 205, adding solvent 102-2 and dissolved catalyst stream 108A to effluent 107 to form mixture 108 wherein the dissolved catalyst stream 108A may be metal organic salts in hydrocarbon base, which is fed to sub reactor 105-2, at block 206.

According to embodiments of the invention, method 20, at block 207, includes hydrogen stream 106-2 and dispersed catalyst stream 106-2A being added to sub reactor 105-2. In embodiments of the invention, hydrogen stream 106-2 comprises a pure hydrogen gas from steam methane reformer or a hydrogen grid or a hydrogen rich stream such as fuel gas stream, cracked gas coming from any refinery/petrochemical unit. The dispersed catalyst stream 106-2A may be a selection from an alkali metal hydroxide or oxide, Ni—Mo oxides or sulphides, Co—Mo oxides or sulphides, W—Mo oxides or sulphides on alumina or zeolites or any combination of these having hydro-processing and/or hydrogen transfer activity. In embodiments of the invention, 0.1 to 15 wt. % content of each type of metal may be present in the dispersed catalyst and supported on alumina, silica or aluminosilcates/zeolites and the metals may be present as oxides or sulphides. According to embodiments of the invention, hydrogen stream 106-2 may be at a temperature, entering sub reactor 105-2, in a range of 50 to 550° C.

According to embodiments of the invention, at block 208, a mixture of mixture 108, dispersed catalyst 106-2A, and hydrogen stream 106-2 (for example, a pure hydrogen gas from steam methane reformer or a hydrogen grid or a hydrogen rich stream such as fuel gas stream, cracked gas coming from any refinery/petrochemical unit) is subjected to reaction conditions in sub reactor 105-2 sufficient to convert hydrocarbon molecules of mixture 108 into smaller molecules (further upgrade of feed 100). According to embodiments of the invention, the further upgrading can be carried out in sub reactor 105-2 at a temperature in a range of 300 to 550° C., preferably in a range of 400 to 470° C. and at a pressure of up to 200 barg, preferably a pressure of 70 barg or less.

At block 209, according to embodiment of the invention, effluent 109 is flowed from sub reactor 105-2. According to embodiments of the invention, conversion of 350+° C. material present in the feed (mixture) to each of sub reactor 105-1, sub reactor 105-2, sub reactor 105-3 is converted to 350–° C. material up to an extent of 100%, alternatively 90%, 80%, 70% and not less than 60%. This conversion can be achieved by sub reactor 105-1, sub reactor 105-2, and/or sub reactor 105-3.

In embodiments of the invention, method 20 involves, at block 210, adding solvent 102-3 and dissolved catalyst stream 110A to effluent 109 to form mixture 110 wherein the dissolved catalyst stream 110A may be metal organic salts in hydrocarbon base; which is fed to sub reactor 105-3, at block 211.

According to embodiments of the invention, method 20, at block 212, includes hydrogen stream 106-3 being added to sub reactor 105-3. In embodiments of the invention, hydrogen stream 106-3 comprises a pure hydrogen gas from steam methane reformer or a hydrogen grid or a hydrogen rich stream such as fuel gas stream, cracked gas coming from any refinery/petrochemical unit. Catalyst stream 106-3A may be a selection from an alkali metal hydroxide or oxide, Ni—Mo oxides or sulphides, Co—Mo oxides or sulphides, W—Mo oxides or sulphides on alumina or zeolites or any combination of these having hydro-processing and/or hydrogen transfer activity. In embodiments of the invention, 0.1 to 15 wt. % content of each type of metal may be present in the dispersed catalyst and supported on alumina, silica or aluminosilcates/zeolites and the metals may be present as oxides or sulphides. According to embodiments of the invention, hydrogen stream 106-3 may be at a temperature, entering sub reactor 105-3, in a range of 50 to 550° C.

According to embodiments of the invention, at block 213, a mixture of mixture 110 and hydrogen stream 106-3 is subjected to reaction conditions in sub reactor 105-3 sufficient to convert hydrocarbon molecules of mixture 110 into smaller molecules (further upgrade of feed 100). According to embodiments of the invention, the further upgrading can be carried out in sub reactor 105-2 at a temperature in a range of 300 to 550° C., preferably in a range of 400 to 470° C., at a pressure of up to 200 barg, preferably a pressure of 70 barg or less. According to embodiments of the invention, solvent is added to keep asphaltene in solution and so that conversion increases as the stage increases (e.g., from sub reactor 105-1, to sub reactor 105-2, to sub reactor 105-3). Feed (each of mixture 104, mixture 108, and mixture 110) is progressively contacted in reactors with increasing volumes to keep the contact time the same or less and catalyst addition rate increases progressively from, for example, sub reactor 105-2, to sub reactor 105-3 to maintain metal concentration. Temperature can be increased from sub reactor 105-1, to sub reactor 105-2, to sub reactor 105-3. According to embodiments of the invention, the severity of processing of feed to the reactor can be continuously increased to get higher conversion.

At block 214, according to embodiments of the invention, effluent 111 is flowed from sub reactor 105-3 to distillation column 112. Effluent 111, in embodiments of the invention, comprises 25 to 30 wt. % paraffin, 27 to 32 wt. % isoparaffin, 0.5 to 0.9 wt. % olefin, 12 to 18 wt. % naphthene, and 18 to 23 wt. % aromatics. In embodiments of the invention, effluent 111 comprises 30 wt. % hydrocarbons that boil above 350° C., alternatively 20 wt. % hydrocarbons that boil above 350° C., alternatively 10 wt. % hydrocarbons that boil above 350° C., alternatively 5 wt. % hydrocarbons that boil above 350° C., or alternatively 1 to 2 wt. % boils above 350° C., or entire effluent boils below 350° C.

As the conversion progresses in sub reactor 105-1, then sub reactor 105-2, and then sub reactor 105-3, the tendency of asphaltenes in solution is to aggregate and precipitate out. According to embodiments of the invention, this tendency is overcome by the creation of a co-feed/solvent mixture (i.e., adding solvent 102-1, solvent 102-2, and solvent 102-3) to keep asphaltenes in solution. Without the addition of the solvent that keeps asphaltene in solution, high conversions of feed results in severe coking and serious operational issues (e.g., plugging). Another purpose is to use a solvent to loosen up/enlarge distances between asphaltene layers to prevent aggregation. It should be noted that, in embodiments of the invention, the amount of solvent (co-feed) added at each stage, namely at sub reactor 105-1, sub reactor 105-2, and sub reactor 105-3 increases. In other words, the amount of solvent 102-2 added to sub reactor 105-2 is greater than the amount of solvent 102-1 added to sub reactor 105-1, and the amount of solvent 102-3 added to sub reactor 105-3 is greater than the amount of solvent 102-2 added to sub reactor 105-2. In sum, according to embodiments of the invention, solvents rich in aromatics and resins are added in stages to maintain these asphaltenes in dissolved form thereby leading to their higher conversion. According to embodiments of the invention, method 20 is carried out in system 10 so that the process liquids are in asphaltene stable conditions with P value greater than 1 and more closer to 1.2. P value is defined as P=1+Xmin (Shell standards SMS 1600-01), where Critical Cetane dilution (Xmin) is the number of mL of Cetane with which 1 g of sample can be diluted until it just does not flocculate the asphaltenes.

According to embodiments of the invention, at block 215, distillation column 112 distills effluent 111 to produce product stream 115 for further upgradation, recycle stream 114 for recycling to any of the previous sub-reactors and purge stream 113 (heavy) for preventing buildup of unwanted solids/coke over a period of time. Operating aqua-processing hydro-processing reactor 105 (collectively sub reactor 105-1, sub reactor 105-2, and sub reactor 105-3) under high severity conditions, including a temperature in a range of 300 to 550° C., preferably 400 to 470° C. and pressure up to 200 barg (typically 70 barg or less), causes product stream 115, the liquid product from this process, to have more than 97 wt. % hydrocarbons that boil below 350° C., with olefin content of the product boiling below 240° C. being less than 1 wt. % as analyzed using ASTM D6730 in a Detailed Hydrocarbon Analyzer (DHA). Also, in embodiments of the invention, the gas product produced does not have any olefins. The liquid product can thus be directly fed to a steam cracker to produce high value chemicals such as ethylene, propylene and benzene. According to embodiments of the invention, purge stream 113 and recycle stream 114 comprise material that boils above 350° C. The flowrate ratio of recycle stream 114 to purge stream 113 is 95:5 by weight. It should be noted that, in embodiments of the invention, catalyst is recycled from downstream distillation column back to the reaction stages (sub reactors) and that the proportion of catalyst recycled can be varied at each stage to manipulate the fresh makeup catalyst addition.

According to embodiments of the invention, aqua-processing hydro-processing reactor 105 produces coke stream 116. In embodiments of the invention where aqua-processing hydro-processing reactor 105 is a fixed bed reactor, coke is burnt during regeneration. In embodiments of the invention where aqua-processing hydro-processing reactor 105 is an ebullated bed, there can be a coke burn step for catalyst. In embodiments of the invention where aqua-processing hydro-processing reactor 105 is a slurry reactor or a bubble column reactor, coke can be removed by purging a small amount of bottom stream from the downstream distillation unit.

Figure 3:
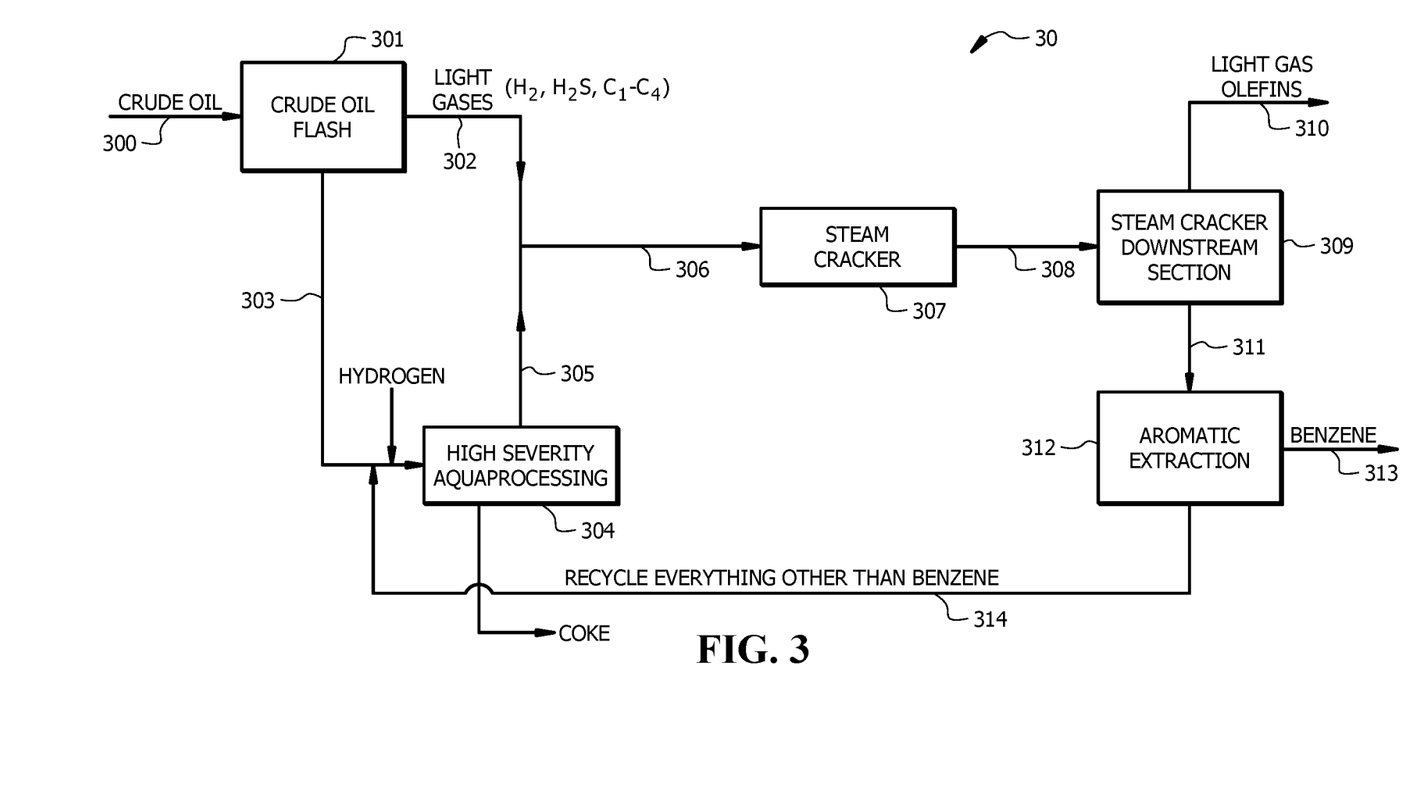
FIG. 3 is a system for aqua-processing hydro-processing crude oil and/or heavy oil and/or residues in combination with a steam cracker unit, according to embodiments of the invention.
Figure 4:
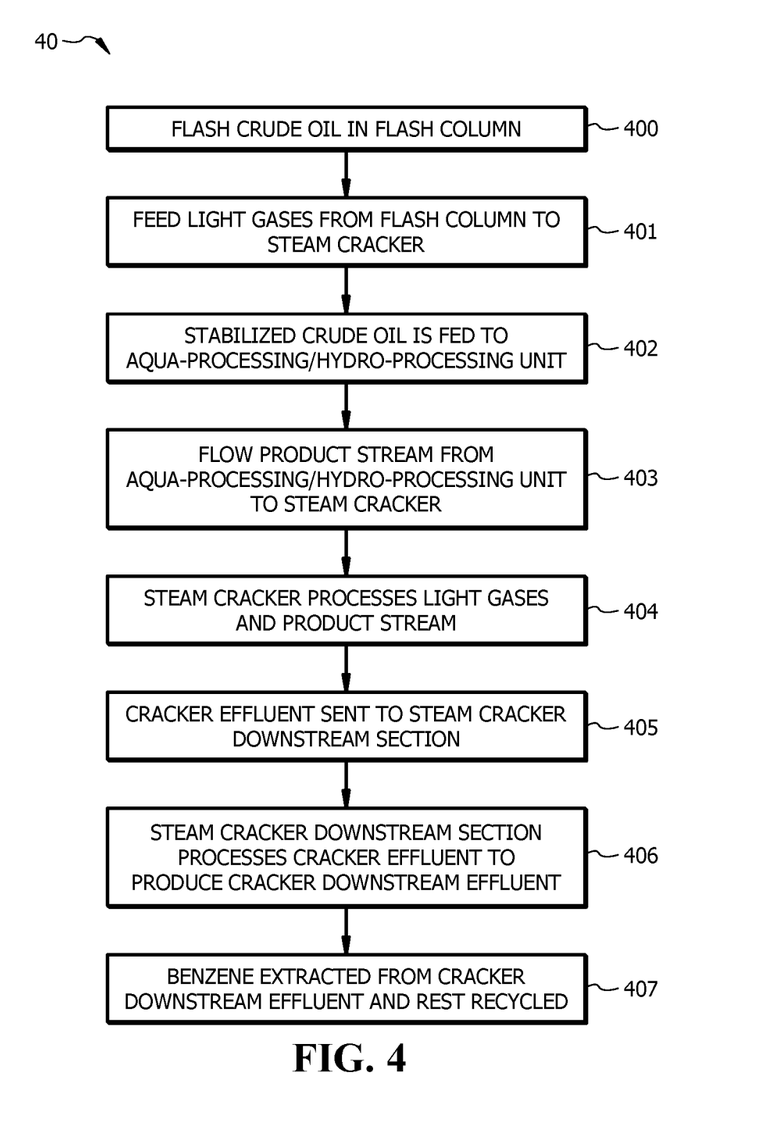
FIG. 4 is a method for aqua-processing hydro-processing crude oil and/or heavy oil and/or residues, according to embodiments of the invention.

FIG. 3 shows system 30 for aqua-processing hydro-processing crude oil and/or heavy oil and/or residues in combination with a steam cracker unit, according to embodiments of the invention. FIG. 4 shows method 40 for aqua-processing hydro-processing crude oil and/or heavy oil and/or residues, according to embodiments of the invention. Method 40 may be implemented using system 30.

In embodiments of the invention, whole crude oil 300 is flashed, at block 400 of method 40, in flash column 301, to separate out light gases inherently present in crude oil 300. It should be noted that in embodiments of the invention the feed to flash column 301 can be heavy oil/residues. In embodiments of the invention, light gases 302 can be fed to a dedicated gas cracker or to mixed feed cracking steam cracker. As shown in FIG. 3 and FIG. 4, in embodiments of the invention, light gases 302 is fed from flash column 301 to steam cracker 307, at block 401. According to embodiments of the invention, light gases 302 typically comprise 0 to 5 wt. % $C_2$, 30 to 40 wt. % $C_3$, 10 to 20 wt. % $C_4$, and 45 to 55, wt. % $nC_4$.

Stabilized crude oil 303 from the bottom of flash column 301, according to embodiments of the invention, is fed to high severity aqua-processing hydro-processing unit 304 (e.g., system 10 described above) to produce gas, liquid and coke products as described in method 20 above, at block 402. In embodiments of the invention, gas product from aqua-processing hydro-processing unit 304 is fed to gas crackers or mixed feed cracking furnace, liquid is fed to liquid steam cracker or mixed feed furnace and purge is used in downstream boilers/gasifiers/any other application which recovers energy value from purge or use of purge for downstream applications like electrodes, blast furnaces etc. In embodiments of the invention, purge is used to generate hydrogen and/or synthesis gas, as fuel, and/or as used as tar component in road construction applications and/or water-proofing. In embodiments of the invention, method 40 includes, at block 403, product stream 305 (at a boiling point temperature in a range of 36 to 350° C.) being flowed with light gases 302 to steam cracker 307.

At block 404, steam cracker 307 cracks light gases 302 and product stream 305 to produce steam cracker effluent stream 308. According to embodiments of the invention, steam cracker 307 is operated to provide the following process reaction conditions: a temperature in a range of 800 to 860° C. coil outlet temperature, a pressure in a range of 0.1 to 3 barg, and 0.1 to 0.5 seconds contact time. According to embodiments of the invention, steam cracker effluent stream 308 comprises 0.5 to 1.5, wt. % hydrogen, 15 to 20, wt. % methane, 35 to 45, wt. % ethylene, 15 to 20, wt. % propylene, 10 to 15 wt. % $C_4$ compounds, 0 to 0.5 wt. % pyrolysis gasoline, 0 to 0.5 wt. % fuel oil, 5 to 10 wt. % benzene, and 5 to 10 wt. % coke.

At block 405, steam cracker effluent is routed to steam cracker downstream section 309, where steam cracker effluent stream 308 is subjected to standard separation technologies known in the art and practiced industrially to produce light gas olefins 310, a paraffin gas stream (not shown in FIG. 3, but is recycled to steam cracker 307), methane and hydrogen stream used as plant fuel or for producing hydrogen (also not shown in FIG. 3) and steam cracker downstream effluent 311, at block 406 to feed to aromatic extraction unit 312 to separate out benzene by known commercial processes. According to embodiments of the invention, steam cracker 307 is operated to provide the following process reaction conditions: a temperature in a range of 800 to 860° C. coil outlet temperature, a pressure in a range of 0.1 to 3 barg, and a contact time of 0.1 to 0.5 seconds. According to embodiments of the invention, light gas olefins 310 comprise 50 to 65, wt. % ethylene, 25 to 30 wt. % propylene, and 15 to 20 wt. % butene. In embodiments of the invention, steam cracker downstream effluent 311 is flowed to aromatic extraction unit 312, which extracts benzene 313 to leave recycle stream 314, at block 407. According to embodiments of the invention, recycle stream 314 comprises 45 to 55 wt. % pyrolysis gasoline and 45 to 55 wt. % fuel oil.

In order to avoid fuel oil or pyrolysis gasoline in products coming out of steam cracker 307, recycle stream 314 is recycled to extinction by feeding it back to aqua-processing hydro-processing unit 304 after extracting higher value benzene. The recycling of recycle stream 314 after extracting benzene to the aqua-processing hydro-processing unit is advantageous as this stream is rich in aromatics and will help in keeping asphaltenes in soluble condition during conversion in aqua-processing hydro-processing unit 304 and reduce fouling in that unit and minimize coke production.

Method 40 can result in ethylene yields in excess of 30 wt. % and the yield of high value chemicals from crude oil (i.e., ethylene, benzene, propylene and butenes/butadienes) can be in excess of 70 wt. %. Further, in embodiments of the invention, the ethylene/propylene yield ratio by mass is above 1.2, preferentially above 1.5 and more preferentially above 2. The methane produced in the process can be used to generate hydrogen. Further, the methane and hydrogen produced in the process can be used as fuel in steam cracking furnace/aqua-processing hydro-processing preheat furnace or for energy value in the utility section in an oil-to-chemicals complex. Also, it is possible to recover hydrogen from the cracked gas products from the steam cracker by feeding a separated mixture of methane and hydrogen through a PSA/membrane unit or any such hydrogen recovery unit. The recovered hydrogen can be used internally in aqua-processing hydro-processing unit 304 while methane gas separated can be used for its energy content in furnaces, produce additional hydrogen utilizing a hydrogen generation unit (Steam Methane Reformer), or used in conversion units like oxidative coupling of methane (OCM) units to produce additional high value ethylene.

Although embodiments of the present invention have been described with reference to blocks of FIG. 2 and FIG. 4, it should be appreciated that operation of the present invention is not limited to the particular blocks and/or the particular order of the blocks illustrated in FIG. 2 and FIG. 4. Accordingly, embodiments of the invention may provide functionality as described herein using various blocks in a sequence different than that of FIG. 2 and FIG. 4.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Demonstration of the Effect of Using Dissolved and Dispersed (Fixed Bed) Catalyst A West Texas blend crude oil residue with a boiling point distribution ranging from 120 to 705° C. was used in this study. The composition of feed in the boiling range of 120 to 240° C. was 25.047 wt. % paraffin, 22.343 wt. % isoparaffin, 0.287 wt. % olefin, 11.727 wt. % naphthene, 16.938 wt. % aromatics, 0.385 wt. % heavies and 23.275 wt. % other unknown hydrocarbon types. The feed had a density of 0.85 g/cc at 30° C. The boiling point distribution of this stream is shown below in Table 1.

TABLE 1

| Boiling Point Distribution of Feed Stream Crude 120+° C. Stream | |
|---|---|
| Mass % | Boiling Point, ° C. |
| IBP | 84.4 |
| 5 | 139.8 |
| 10 | 162.8 |
| 15 | 183.2 |
| 20 | 204.2 |
| 25 | 222.4 |
| 30 | 240.2 |
| 35 | 258.8 |
| 40 | 278 |
| 45 | 298 |
| 50 | 315.4 |
| 55 | 338.4 |
| 60 | 362 |
| 65 | 390.6 |
| 70 | 424.6 |
| 75 | 466.4 |
| 80 | 499 |
| 85 | 526.8 |
| 90 | 560.2 |
| 95 | 611.2 |
| 99 | 687.4 |
| 100 | 705.6 |

The reactor used in the study was a fixed bed reactor located inside a 3-zone split-tube furnace. The reactor's internal diameter was 13 mm with a concentrically located thermowell of 3.17 mm outer diameter. The reactor was 91.3 cm in length. A commercial hydrotreating catalyst of Co—Ni—Mo on alumina in combination with a hydrocracking catalyst aimed at naphtha/jet fuel range product (10 g bone dry weight each) was broken along the length to particles of 1.5 mm in length and diluted with SiC in the ratio of 62% SiC to 38% catalyst to give a mean particle diameter of 0.31 mm. This was done to avoid slip through of the feed due to wall slip or channeling in the small diameter reactor. Preheating of the bed and post-catalyst inert beds was provided in the form of 3 mm inert alumina beads. The catalyst bed temperature was controlled to isothermal by varying the controlled furnace zone skin temperatures. The fixed bed hydro-processing catalyst (a layered mixture of hydrotreating catalyst and hydrocracking catalyst) was sulphided using 3 wt. % S in n-hexadecane (sulphur was introduced as dimethyl disulphide) with an upflow of sulphiding feed in the reactor up to a final sulphiding temperature of 460° C. Following sulphiding of the catalyst, the 120+° C. boiling residue from West Texas blend crude oil was doped with 2 wt. % S and 800 ppm each of Ni and Mo doped as metal octanoate (dissolved catalysts for better hydrogen uptake and enhanced hydrogenation activity) was fed to the reactor. The reactor was maintained at the operating conditions with a weight hourly space velocity (WHSV) of 1 hr$^{-1}$, a H$_2$/HC ratio of 400 NL/L of liquid feed (H$_2$ gas with a flow rate of 9.4 NL/h), a pressure of 40.8 barg (600 psig) and catalyst bed temperature of 450° C. The reactor effluent gases (e.g., a hydrocarbon product) were cooled to condense the liquids (i.e., treated hydrocarbon stream in the form of a liquid product) under pressure while allowing non-condensed gases (e.g., methane, ethane, hydrogen sulphide, or combinations thereof) to separate as a gas product and flow to a wet gas meter after scrubbing with a caustic solution. The effluent gas flow from the caustic scrubber was analyzed using a refinery gas analyzer Gas Chromatograph (a custom gas analyzer from M/s AC Analytical Controls BV). The liquid product obtained from the packed bed reactor was analyzed by a Simulated Distillation (SIMDIS) gas chromatograph for boiling point distribution as shown in Table 2. SIMDIS results indicated 97% of product boiled below 350° C. starting from a feed having an end boiling point above 700° C. The liquid was further analyzed by a Detailed Hydrocarbon Analyzer (ASTM D6730) and had a PIONA composition of the product boiling below 240° C. as shown in Table 3 with olefins in the liquid product at <1 wt. % concentration.

The reactor effluent gas analysis indicates an absence of olefins in the gas products as shown in Table 4.

TABLE 4

| Gas Analysis | |
| --- | --- |
| Gas Components | Mole % |
| $C_1$, mol. % | 6.8 |
| $C_2$-$C_4$ Saturates, mol. % | 3.8 |
| $C_2$-$C_4$ olefins, mol. % | 0.0 |

Example 2

Effect of Using Only Dispersed (Fixed Bed) Catalyst

The same feed and process conditions and same reactor as mentioned in Example 1 above were used in this study, with the difference being that only fixed bed catalyst as in Example 1 was used and the feed did not contain dissolved catalysts as used in Example 1. The SIMDIS results from this study indicated that approximately 97% product still boiled below 350° C. as shown below in the Table 5.

TABLE 5

| SIMDIS Results | | |
| --- | --- | --- |
| Mass % | West Texas Crude oil 120+° C. residue used as feed Boiling Point (BP), ° C. | Liquid Product from Example 2 BP, ° C. |
| IBP | 84.4 | 42.8 |
| 5 | 139.8 | 84.4 |
| 10 | 162.8 | 122.4 |
| 15 | 183.2 | 136 |
| 20 | 204.2 | 152.4 |
| 25 | 222.4 | 162.8 |
| 30 | 240.2 | 175.8 |
| 35 | 258.8 | 188.6 |
| 40 | 278 | 199.2 |
| 45 | 298 | 213.4 |
| 50 | 315.4 | 222.2 |
| 55 | 338.4 | 233.6 |
| 60 | 362 | 245 |
| 65 | 390.6 | 255.8 |
| 70 | 424.6 | 269.6 |
| 75 | 466.4 | 282.4 |
| 80 | 499 | 293 |
| 85 | 526.8 | 304.8 |
| 90 | 560.2 | 317.4 |
| 95 | 611.2 | 337.4 |
| 99 | 687.4 | 366.6 |
| 100 | 705.6 | 379.8 |

The PIONA results indicated that liquid product boiling below 240° C. has about 1.8 wt. % olefins in contrast to Example 1 where dissolved catalyst was also used for better hydrogen uptake as shown below in Table 6.

TABLE 2

| Boiling Point Distribution of Feed and Liquid Product | | |
| --- | --- | --- |
| Mass % | West Texas Crude oil 120+° C. residue used as feed Boiling Point (BP), ° C. | Liquid Product BP, ° C. |
| IBP | 84.4 | 35 |
| 5 | 139.8 | 84.4 |
| 10 | 162.8 | 102 |
| 15 | 183.2 | 112.2 |
| 20 | 204.2 | 122.4 |
| 25 | 222.4 | 136 |
| 30 | 240.2 | 151 |
| 35 | 258.8 | 162.8 |
| 40 | 278 | 176.4 |
| 45 | 298 | 192 |
| 50 | 315.4 | 202.8 |
| 55 | 338.4 | 217.6 |
| 60 | 362 | 229.8 |
| 65 | 390.6 | 245.4 |
| 70 | 424.6 | 263.4 |
| 75 | 466.4 | 284.2 |
| 80 | 499 | 286.4 |
| 85 | 526.8 | 287.4 |
| 90 | 560.2 | 305.8 |
| 95 | 611.2 | 331.8 |
| 99 | 687.4 | 377.4 |
| 100 | 705.6 | 390.2 |

TABLE 3

| Detailed Hydrocarbon Analysis of Liquid Product and Feed With BP Below 240° C. | | | | | | | | |
| --- | --- | --- | --- | --- | --- | --- | --- | --- |
| S.No. | Sample | P | I | O | N | A | Heavies | Unknowns |
| 1 | Feed | 25.047 | 22.343 | 0.287 | 11.727 | 16.938 | 0.385 | 23.275 |
| 2 | Liquid Product | 22.527 | 29.425 | 0.684 | 12.851 | 17.585 | 0.29 | 16.637 |

TABLE 6

Detailed Hydrocarbon Analysis of Liquid Product and Feed Boiling Below 240° C.

| S.No. | Sample | P | I | O | N | A | Heavies | Unknowns |
|---|---|---|---|---|---|---|---|---|
| 1 | Feed | 25.047 | 22.343 | 0.287 | 11.727 | 16.938 | 0.385 | 23.275 |
| 2 | Liquid Product | 27.428 | 18.41 | 1.768 | 9.139 | 14.776 | 5.503 | 22.972 |

Example 3

Effect of Using Only Dissolved Catalyst

The same feed and process conditions as mentioned above in Example 1 were used in this study, with the difference being that the feed has dissolved Ni and Mo octanoates at concentrations mentioned in Example 1. The reactor had only a bed of inert alumina and no fixed bed catalyst. The SIMDIS results for this study are as shown below in Table 7.

TABLE 7

SIMDIS Results

| Mass % | West Texas Crude oil 120+° C. residue used as feed Boiling Point (BP), ° C. | Liquid Product from Example 3 BP, ° C. |
|---|---|---|
| IBP | 84.4 | 36 |
| 5 | 139.8 | 84.4 |
| 10 | 162.8 | 102 |
| 15 | 183.2 | 112.2 |
| 20 | 204.2 | 128.4 |
| 25 | 222.4 | 139.8 |
| 30 | 240.2 | 151 |
| 35 | 258.8 | 158.4 |
| 40 | 278 | 168.8 |
| 45 | 298 | 176.4 |
| 50 | 315.4 | 186 |
| 55 | 338.4 | 195.6 |
| 60 | 362 | 204.6 |
| 65 | 390.6 | 214.6 |
| 70 | 424.6 | 221 |
| 75 | 466.4 | 229.8 |
| 80 | 499 | 238.2 |
| 85 | 526.8 | 249.8 |
| 90 | 560.2 | 261.8 |
| 95 | 611.2 | 279.8 |
| 99 | 687.4 | 314.8 |
| 100 | 705.6 | 339.6 |

The PIONA results of liquid product boiling below 240° C. are shown in Table 8.

TABLE 8

DHA Results for Liquid Products Boiling Below 240° C.

| S.No. | Sample | P | I | O | N | A | Heavies | Unknowns |
|---|---|---|---|---|---|---|---|---|
| 1 | Feed | 25.047 | 22.343 | 0.287 | 11.727 | 16.938 | 0.385 | 23.275 |
| 2 | Liquid Product | 29.661 | 21.636 | 4.005 | 11.308 | 11.474 | 0.214 | 21.702 |

Even though the liquid product boils below 350° C., based on DHA analysis it appears that liquid product has olefins (4 wt. %) higher than steam cracker feed (1 wt. % olefins) requirements.

Example 4

Effect of Using Dissolved Catalyst and Steam

The same feed and process conditions as mentioned in Example 1 were used in this study with the difference being feed has dissolved Ni and Mo octanoates at concentrations mentioned in Example 1 and water was injected in the reactor along with hydrocarbon feed in the ratio of 1:7 water:hydrocarbon on a weight basis. The reactor had only a bed of inert alumina and no fixed bed catalyst. The SIMDIS results indicate a drastic reduction in boiling points with final boiling point of product at 316° C. as shown below in Table 9.

TABLE 9

SIMDIS Results

| Mass % | West Texas Crude oil 120+° C. residue used as feed Boiling Point (BP), ° C. | Liquid Product from Example 4 BP, ° C. |
|---|---|---|
| IBP | 84.4 | 42.8 |
| 5 | 139.8 | 84.4 |
| 10 | 162.8 | 102 |
| 15 | 183.2 | 112.2 |
| 20 | 204.2 | 128.4 |
| 25 | 222.4 | 139.8 |
| 30 | 240.2 | 152.4 |
| 35 | 258.8 | 159.8 |
| 40 | 278 | 170.2 |
| 45 | 298 | 177.8 |
| 50 | 315.4 | 187.4 |
| 55 | 338.4 | 197.6 |
| 60 | 362 | 205 |
| 65 | 390.6 | 216.4 |
| 70 | 424.6 | 221.6 |
| 75 | 466.4 | 231.2 |
| 80 | 499 | 239.2 |
| 85 | 526.8 | 250.8 |

TABLE 9-continued

SIMDIS Results

| Mass % | West Texas Crude oil 120+° C. residue used as feed Boiling Point (BP), ° C. | Liquid Product from Example 4 BP, ° C. |
|---|---|---|
| 90 | 560.2 | 261.6 |
| 95 | 611.2 | 276.4 |
| 99 | 687.4 | 303.4 |
| 100 | 705.6 | 315.8 |

However, the DHA results indicated that the liquid product has an olefin concentration (approximately 4 wt. %) higher than the steam cracker feed (1 wt. % olefins) requirements as shown in Table 10 below.

TABLE 10

DHA Results for Liquid Products Boiling Below 240° C.

| S.No. | Sample | P | I | O | N | A | Heavies | Unknowns |
|---|---|---|---|---|---|---|---|---|
| 1 | Feed | 25.047 | 22.343 | 0.287 | 11.727 | 16.938 | 0.385 | 23.275 |
| 2 | Liquid Product | 24.692 | 19.407 | 4.1 | 9.359 | 11.677 | 6.451 | 24.314 |

The above examples suitably demonstrate the effects of dissolved catalyst, dispersed catalyst and steam. Use of all three components hence appears beneficial for producing liquid products with reduced boiling point and of quality meeting steam cracker feed specifications for olefin content.

Example 5

Effect of Using Whole Crude Oil (Effect of Solvent), Dissolved and Dispersed Catalyst, and Higher Hydrogen Pressure The feed used in this study was whole crude oil instead of 120+° C. residue used in previous examples. The process conditions were a reactor catalyst bed temperature of 450° C., a reactor pressure of 50 barg, a WHSV of 1 hr$^{-1}$ and a H$_2$/HC ratio of 1200 NL/L liquid feed (H$_2$ flow rate 27.5 NLPH). This can represent a system where an asphaltene rich feed (for example 120+° C. residue feed can be considered asphaltene rich in comparison to 120-° C. feed) is in combination with asphaltene lean feed. Also, operating pressure is 10 barg higher than in previous examples and H$_2$/HC ratio is thrice the ratio used in previous examples. This, in general, is a more severe condition in which higher conversion and as a result higher coke deposit from asphaltenes are possible. However, since whole crude oil with more solvency power to keep asphaltene in solution is used, reduced coke is expected even though conversions could be higher.

The SIMDIS results for this study shown in Table 11 below indicate a substantially higher reduction in boiling point with 99% of product now boiling at approximately 293° C. Thus, there is a merit in utilizing higher reactor operating pressures and/or hydrogen to hydrocarbon ratio to cut down on the boiling point of products. While a commercial hydrocracking process operates at approximately 175-200 barg and one may go for the same pressures in the process disclosed here, what has been demonstrated here is a conversion of whole crude oil or residues to low boiling products which can be fed to steam cracker directly without a need for further cracking at low to moderate pressures. So, a pressure of 40-100 barg, preferentially pressures of up to 70 barg can offer the boiling point reductions in crude oil which make them amenable for feeding to steam cracker thus simplifying/intensifying the bottoms upgradation processes for crude oil with potential for low investment costs. Lower pressures than 40 barg can also be used. However, as reactor pressure is reduced, an increase in coke deposits and loss of higher quantity of feed as coke is expected.

TABLE 11

SIMDIS Results

| Mass % | West Texas Crude oil 120+° C. residue used as feed Boiling Point (BP), ° C. | Liquid Product from Example 5 BP, ° C. |
|---|---|---|
| IBP | 84.4 | 36 |
| 5 | 139.8 | 65.4 |
| 10 | 162.8 | 84.4 |
| 15 | 183.2 | 84.4 |
| 20 | 204.2 | 84.4 |
| 25 | 222.4 | 102 |
| 30 | 240.2 | 122.4 |
| 35 | 258.8 | 132.2 |
| 40 | 278 | 136 |
| 45 | 298 | 139.8 |
| 50 | 315.4 | 158.4 |
| 55 | 338.4 | 167.4 |
| 60 | 362 | 192 |
| 65 | 390.6 | 258.6 |
| 70 | 424.6 | 275.4 |
| 75 | 466.4 | 284.2 |
| 80 | 499 | 286.8 |
| 85 | 526.8 | 288.2 |
| 90 | 560.2 | 289.4 |
| 95 | 611.2 | 290.2 |
| 99 | 687.4 | 292.2 |
| 100 | 705.6 | 324.2 |

Example 6

Effect of Use of Water on Coke Make

The study was carried out as mentioned in Example 1 and was compared with another study wherein the catalyst and conditions were maintained the same as in Example 1 except that water was added to the reactor in the ratio of 1:7 water to hydrocarbon by weight. The results of this comparison are shown below.

TABLE 12

| Yield Wt. % | Example 1 | Example 6 With Addition of Water |
|---|---|---|
| Gas | 10.8 | 17.3 |
| Liquid | 84.4 | 79.5 |
| Coke | 4.8 | 3.2 |

The PIONA analysis of liquid product boiling below 240° C. in both cases is as provided in Table 13.

TABLE 13

| | Hydrogen Consumption Wt. % of Feed |
|---|---|
| Example 1 | 2.8 |
| Example 6 | 1.5 |

The crackable hydrocarbon in the product is compared with Example 1 in Table 15 below.

TABLE 15

| | Example 1 | Example 6 |
|---|---|---|
| Liquid Product | 84.4 | 79.5 |
| Gas | 5 | 8 |
| Total | 89.4 | 87.5 |

Crackable hydrocarbon is defined as a product which can be cracked further down. Addition of water suppresses coke, makes slightly lower crackable carbon and slightly higher gas formation.

Example 7

Effect of Aqua-processing Hydro-processing Concept

This example was constructed to demonstrate the beneficial effect of the aqua-processing hydro-processing concept in association with a steam cracker to produce high yields of high value chemicals, namely ethylene, propylene, benzene and butenes. The combination of a flash tower with an aqua-processing hydro-processing unit and steam cracker unit is shown in FIG. 3. The feed crude oil is flashed in a crude flash tower where the objective is to remove only $H_2$, $H_2S$, and $C_1$-$C_4$ hydrocarbons from the liquid feed, after caustic scrubbing/any other means for removal of $H_2S$ is fed to gas crackers or mixed feed furnaces to maximize conversion to ethylene. The stabilized crude oil from the bottom of the flash tower is fed to the aqua-processing hydro-processing unit to produce a liquid product more than 97 wt. % which boils below 350° C. Gas product from this unit feeds the gas cracker as above and liquid products feed liquid steam cracker or a mixed feed furnace. Fuel oil and pyrolysis gasoline produced in the steam cracking process is subjected to benzene extraction and the balance material is recycled back to the aqua-processing hydro-processing unit to extinction. This recycle not only helps in maximizing the desired products but also helps in increasing the aromatic content in the aqua-processing hydro-processing unit which will help in keeping asphaltenes in solution.

Mass balances indicated in Table 16 after accounting for recycle stream indicate that a typical yield of approximately 38 wt. % ethylene, 18 wt. % propylene, 12 wt. % butenes and 7.5 wt. % benzene can be realized. This takes the yield of these high value chemicals to approximately 75 wt. % of whole crude oil. The benefit of this process is the ethylene to propylene ratio is approximately 2.1 which is very high for producing chemicals to crude oils.

TABLE 16

| Mass Balances | | |
|---|---|---|
| Products | MTD | Wt % of product |
| H2 | 600 | 1.0 |
| Methane | 10049 | 16.7 |
| Ethylene | 22718 | 37.8 |
| Propylene | 10941 | 18.2 |
| C4 | 7083 | 11.8 |
| Py Gas | 0 | 0.0 |
| Fuel oil | 0 | 0.0 |
| Benzene | 4498 | 7.5 |
| Coke (MTD) | 4195 | 7.0 |
| Total Products ---> | 60085 | |
| Feed | MTD | |
| H2 consumption | 2971 | |
| Feed crude oil | 57114 | |
| Total Feed ---> | 60085 | |
| Gas feed to Steam cracker (MTD) including recycle from the crude oil feed | | |
| Ethane | 60 | |
| Propane | 365 | |
| i-butane | 147 | |
| n-butane | 442 | |

The loss of coke in the integrated petrochemical complex in which this disclosed concept is used is shown in the above table as approximately 7 wt. % which is typical of fuel and loss numbers typical in refineries. The yield of $H_2$ at 1 wt. % can be separated from the product gases to partly meet the hydrogen demand in the aqua-processing hydro-processing unit while the balance requirement can be met by a hydrogen generation unit. Methane produced in the process can go towards meeting the furnace heating requirements in the process or any spare methane available can be used in hydrogen generation units or can be used as a feed in downstream oxidative coupling of methane unit (OCM) to produce additional ethylene or for making syngas. Coke can be utilized as a fuel for generating steam, heat or can be used to produce syngas, for electrode applications after further treatment or as a tar component in road constructions.

In the context of the present invention, at the least the following 20 embodiments are described. Embodiment 1 is a method of processing hydrocarbons. The method includes subjecting a mixture comprising (1) a feedstock of crude oil and/or heavy oil and/or residues, (2) steam, (3) hydrogen, (4) a catalyst, and (5) a solvent selective for dissolving asphaltene, in a processing unit, to conditions sufficient to convert at least some hydrocarbon molecules of the feedstock to molecules that have less carbon atoms than the at least some hydrocarbon molecules. In addition, the method includes recovering, from the processing unit, intermediate product streams containing: (1) a gas stream that comprises primarily $C_1$ to $C_4$ hydrocarbons and (2) a liquid stream that comprises primarily saturates. The method further includes cracking the liquid stream to produce one or more of ethylene, propylene, butene, and benzene. Embodiment 2 is the method of embodiment 1, wherein the processing unit includes a reactor unit and a separation unit and the method further includes, prior to the subjecting step, flowing (1) the feedstock of crude oil and/or heavy oil and/or residues, (2) the steam, (3) the hydrogen, (4) the catalyst, and (5) the solvent, to the reactor unit, wherein the subjecting step is carried out in the reactor unit, then flowing effluent from the reactor unit to the separation unit, wherein the separation unit contains a distillation column, and distilling the effluent from the reactor unit, in the distillation column, to produce: (1) the gas stream and (2) the liquid stream. Embodiment 3 is the method of embodiment 2, wherein the reactor unit includes a plurality of reactors and the subjecting step includes subjecting a mixture containing the feedstock of crude oil and/or heavy oil and/or residues, the steam, a first portion of the hydrogen, a first portion of the catalyst, and a first portion of the solvent in a first reactor of the plurality or reactors, to reaction conditions sufficient to convert at least some hydrocarbon molecules of the feedstock to molecules that have less carbon atoms than the at least some hydrocarbon molecules of the feedstock. The method further includes flowing first reactor effluent from the first reactor to a second reactor of the plurality of reactors, and subjecting the first reactor effluent, a second portion of the hydrogen, a second portion of the catalyst, and a second portion of the solvent, in the second reactor of the plurality of reactors, to reaction conditions sufficient to convert at least some hydrocarbon molecules of the first reactor effluent to molecules that have less carbon atoms than the at least some hydrocarbon molecules of the first reactor effluent. Embodiment 4 is the method of embodiment 3, wherein the reactor unit includes two reactors and a second reactor effluent is the effluent from the reactor unit. Embodiment 5 is the method of embodiment 3, further including flowing a second reactor effluent from the second reactor to a third reactor of the plurality of reactors. The method further includes subjecting the second reactor effluent, a third portion of the hydrogen, a third portion of the catalyst, and a third portion of the solvent, in the third reactor of the plurality of reactors, to reaction conditions sufficient to convert at least some hydrocarbon molecules of the second reactor effluent to molecules that have less carbon atoms than the at least some hydrocarbon molecules of the second reactor effluent. Embodiment 6 is the method of embodiment 5, wherein the reactor unit contains three reactors and a third reactor effluent is the effluent from the reactor unit. Embodiment 7 is the method of any of embodiments 1 to 6, wherein the catalyst includes a dissolved portion and a dispersed portion. Embodiment 8 is the method of embodiment 7, wherein the dissolved portion of the catalyst contains an organometallic compound having one or more of Ni, Mo, Co, W, Zr. Embodiment 9 is the method of either of embodiments 7 or 8, wherein the dissolved portion of the catalyst comprises metal naphthenates and/or octanoates having hydrogenation activity. Embodiment 10 is the method of embodiment 7, wherein the dispersed portion of the catalyst is a selection from the list consisting of an alkali metal hydroxide or oxide, Ni—Mo oxides or sulphides, Co—Mo oxides or sulphides, W—Mo oxides or sulphides on alumina or zeolites or any combination of these having hydro-processing and/or hydrogen transfer activity. Embodiment 11 is the method of any of embodiments 1 to 10, wherein the hydrogen is provided by a hydrogen rich stream comprising fuel gas. Embodiment 12 is the method of any of embodiments 2 to 11, wherein the hydrogen is maintained at a pressure of up to 200 barg and more preferentially up to 70 barg in the reactor unit. Embodiment 13 is the method of any of embodiments 1 to 12, wherein the solvent contains primarily aromatics, and resins. Embodiment 14 is the method of any of embodiments 1 to 12, wherein asphaltenes are stable, having P value greater than 1. Embodiment 15 is the method of any of embodiments 2 to 14, wherein steam is supplied to the processing unit at a flow rate that is at least more than 0.2% of the flow rate of the hydrogen. Embodiment 16 is the method of any of embodiments 1 to 15, wherein the ethylene/propylene yield ratio by mass is above 1.2, preferentially above 1.5 and more preferentially above 2 and ethylene yield is above 35 wt. %. Embodiment 17 is the method of any of embodiments 1 to 16, wherein the cracking further produces methane. Embodiment 18 is the method of embodiment 17, wherein the methane is used to generate hydrogen. Embodiment 19 is the method of embodiment 17, wherein the methane is used to generate additional ethylene through methane coupling. Embodiment 20 is the method of any of embodiments 1 to 16, wherein the solvent is provided in the mixture in a quantity sufficient to keep at least 90 wt. % of asphaltenes from the feedstock in solution.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of processing hydrocarbons, the method comprising:
   subjecting a mixture comprising (1) a feedstock of crude oil and/or heavy oil and/or residues, (2) steam, (3) hydrogen, (4) a catalyst, and (5) a solvent selective for dissolving asphaltene, in a processing unit, to conditions sufficient to convert at least some hydrocarbon molecules of the feedstock to molecules that have less carbon atoms than the at least some hydrocarbon molecules;
   recovering, from the processing unit, intermediate product streams comprising: (1) a gas stream that comprises primarily $C_1$ to $C_4$ hydrocarbons and (2) a liquid stream that comprises primarily saturates; and
   cracking the liquid stream to produce one or more of ethylene, propylene, butene, and benzene;
   wherein the solvent is provided in the mixture in a quantity sufficient to keep at least 90 wt. % of asphaltenes from the feedstock in solution.

2. The method of claim 1, wherein the processing unit comprises a reactor unit and a separation unit and the method further comprises:
   prior to the subjecting step, flowing (1) the feedstock of crude oil and/or heavy oil and/or residues, (2) the steam, (3) the hydrogen, (4) the catalyst, and (5) the solvent, to the reactor unit, wherein the subjecting step is carried out in the reactor unit;
   flowing effluent from the reactor unit to the separation unit, wherein the separation unit comprises a distillation column;

distilling the effluent from the reactor unit, in the distillation column, to produce: (1) the gas stream and (2) the liquid stream.

3. The method of claim 2, wherein the reactor unit comprises a plurality of reactors and the subjecting step comprises:
subjecting a mixture comprising the feedstock of crude oil and/or heavy oil and/or residues, the steam, a first portion of the hydrogen, a first portion of the catalyst, and a first portion of the solvent in a first reactor of the plurality or reactors, to reaction conditions sufficient to convert at least some hydrocarbon molecules of the feedstock to molecules that have less carbon atoms than the at least some hydrocarbon molecules of the feedstock;
flowing first reactor effluent from the first reactor to a second reactor of the plurality of reactors;
subjecting the first reactor effluent, a second portion of the hydrogen, a second portion of the catalyst, and a second portion of the solvent, in the second reactor of the plurality of reactors, to reaction conditions sufficient to convert at least some hydrocarbon molecules of the first reactor effluent to molecules that have less carbon atoms than the at least some hydrocarbon molecules of the first reactor effluent.

4. The method of claim 3, wherein the reactor unit comprises two reactors and a second reactor effluent is the effluent from the reactor unit.

5. The method of claim 3, further comprising:
flowing a second reactor effluent from the second reactor to a third reactor of the plurality of reactors:
subjecting the second reactor effluent, a third portion of the hydrogen, a third portion of the catalyst, and a third portion of the solvent, in the third reactor of the plurality of reactors, to reaction conditions sufficient to convert at least some hydrocarbon molecules of the second reactor effluent to molecules that have less carbon atoms than the at least some hydrocarbon molecules of the second reactor effluent.

6. The method of claim 5, wherein the reactor unit comprises three reactors and a third reactor effluent is the effluent from the reactor unit.

7. A method of processing hydrocarbons, the method comprising:
subjecting a mixture comprising (1) a feedstock of crude oil and/or heavy oil and/or residues, (2) steam, (3) hydrogen, (4) a catalyst, and (5) a solvent selective for dissolving asphaltene, in a processing unit, to conditions sufficient to convert at least some hydrocarbon molecules of the feedstock to molecules that have less carbon atoms than the at least some hydrocarbon molecules;
recovering, from the processing unit, intermediate product streams comprising: (1) a gas stream that comprises primarily $C_1$ to $C_4$ hydrocarbons and (2) a liquid stream that comprises primarily saturates; and
cracking the liquid stream to produce one or more of ethylene, propylene, butene, and benzene, wherein the catalyst comprises a dissolved portion and a dispersed portion.

8. The method of claim 7, wherein the dissolved portion of the catalyst comprises an organometallic compound comprising.

9. A method of processing hydrocarbons, the method comprising:
subjecting a mixture comprising (1) a feedstock of crude oil and/or heavy oil and/or residues, (2) steam, (3) hydrogen, (4) a catalyst, and (5) a solvent selective for dissolving asphaltene, in a processing unit, to conditions sufficient to convert at least some hydrocarbon molecules of the feedstock to molecules that have less carbon atoms than the at least some hydrocarbon molecules;
recovering, from the processing unit, intermediate product streams comprising: (1) a gas stream that comprises primarily $C_1$ to $C_4$ hydrocarbons and (2) a liquid stream that comprises primarily saturates; and
cracking the liquid stream to produce one or more of ethylene, propylene, butene, and benzene, wherein the catalyst comprises a dissolved portion and a dispersed portion; and
wherein the dissolved portion of the catalyst comprises metal naphthenates and/or octanoates having hydrogenation activity.

10. The method of claim 7, wherein the dispersed portion of the catalyst is an alkali metal hydroxide or oxide having hydro-processing and/or hydrogen transfer activity.

11. The method of claim 1, wherein the hydrogen is provided by a hydrogen rich stream comprising fuel gas.

12. The method of claim 2, wherein the hydrogen is maintained at a pressure of up to 200 barg up to 70 barg in the reactor unit.

13. The method of claim 1, wherein the solvent comprises.

14. The method of claim 1, wherein asphaltenes are stable, having P value greater than 1.

15. The method of claim 2, wherein steam is supplied to the processing unit at a flow rate that is at least more than 0.2% of the flow rate of the hydrogen.

16. The method of claim 1, wherein the ethylene/propylene yield ratio by mass is above 1.2 and ethylene yield is above 35 wt. %.

17. The method of claim 1, wherein the cracking further produces methane.

18. The method of claim 17, wherein the methane is used to generate hydrogen.

19. The method of claim 17, wherein the methane is used to generate additional ethylene through methane coupling.

20. The method of claim 2, wherein the hydrogen is maintained at a pressure of up to 70 barg.

* * * * *

UNITED STATES PATENT AND TRADEMARK OFFICE
CERTIFICATE OF CORRECTION

PATENT NO. : 11,680,028 B2
APPLICATION NO. : 17/422784
DATED : June 20, 2023
INVENTOR(S) : Ravichander Narayanaswamy et al.

Page 1 of 1

It is certified that error appears in the above-identified patent and that said Letters Patent is hereby corrected as shown below:

In the Claims

At Column 24, Claim number 8, Line number 7, add --Zr-- after "comprising".
At Column 24, Claim number 13, Line number 38, add --resins-- after "comprises".

Signed and Sealed this
Fifteenth Day of August, 2023

Katherine Kelly Vidal
*Director of the United States Patent and Trademark Office*